United States Patent [19]
Owens et al.

[11] Patent Number: 6,056,697
[45] Date of Patent: May 2, 2000

[54] PRESSURE CATHETER CALIBRATION CHAMBER

[75] Inventors: Richard Owens; Robert Persky; Gary W. Muniz, all of San Antonio, Tex.; Steven C. Koenig, Floyds Knobs, Ind.; Craig A. Reister, San Antonio, Tex.

[73] Assignee: The United States of America as represented by the Secretary of the Air Force, Washington, D.C.

[21] Appl. No.: 08/939,345

[22] Filed: Sep. 29, 1997

Related U.S. Application Data

[60] Provisional application No. 60/027,840, Oct. 4, 1996.

[51] Int. Cl.$^7$ ....................................................... A61B 5/02
[52] U.S. Cl. ........................................... 600/485; 600/488
[58] Field of Search ................................... 600/485, 486, 600/488; 73/1.35, 1.57, 1.67

[56] References Cited

U.S. PATENT DOCUMENTS

| | | | |
|---|---|---|---|
| 3,122,136 | 2/1964 | Murph, Jr. | 600/485 |
| 4,342,218 | 8/1982 | Fox | 73/1.62 |
| 4,384,470 | 5/1983 | Fiore | 73/1.68 |
| 4,459,841 | 7/1984 | Hok et al. | 73/753 |
| 4,610,256 | 9/1986 | Wallace | 600/488 |
| 5,273,047 | 12/1993 | Tripp et al. | 600/488 |

*Primary Examiner*—Cary O'Connor
*Assistant Examiner*—Nayin Natnithithadha
*Attorney, Agent, or Firm*—Tony Y. Cole; Bobby D. Scearce; Thomas L. Kundert

[57] ABSTRACT

An apparatus and method for calibrating the pressure readings obtained by catheter tip pressure transducers. The apparatus includes a Plexiglas vessel covered by a closure containing eight catheter ports through which the transducers are introduced into the vessel. The vessel is filled with saline solution that has been warmed to body temperature. The transducer ends of the catheters are inserted through airtight hemostatic control valves into the vessel through the catheter ports. Plexiglas guide tubes are used to guide the transducers into the saline solution at predetermined distances below the surface of the saline solution. The distances are used to calculate the hydrostatic pressures exerted upon the transducers by the saline solution. Known pressures are applied to the transducers through an airtight pressure port in the closure. Calculated hydrostatic pressures are added to the known pressures to provide calibration pressures for comparison with monitored pressure readings.

12 Claims, 3 Drawing Sheets

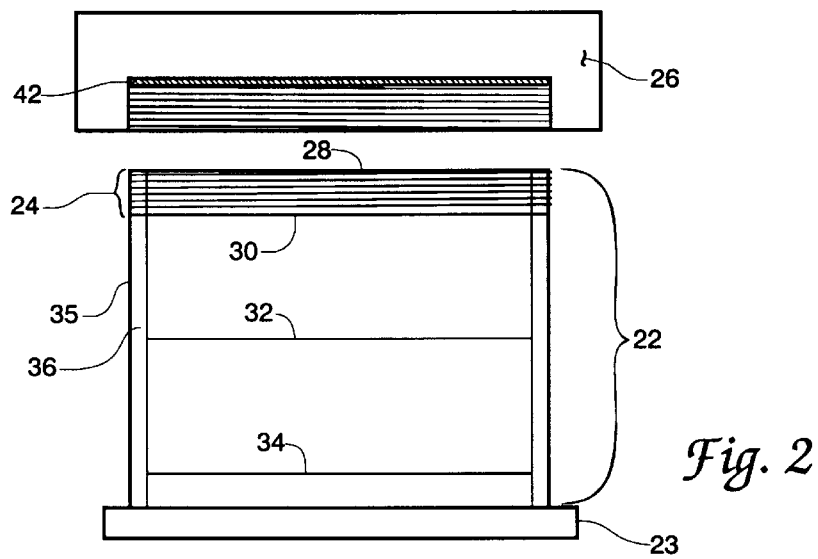
Fig. 2
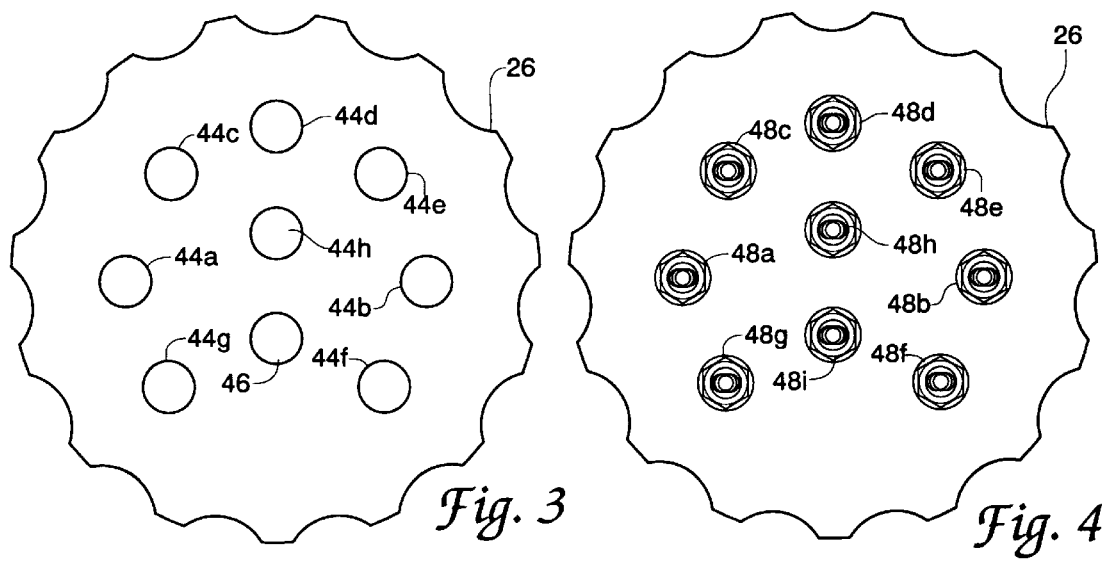
Fig. 3
Fig. 4

PRESSURE CATHETER CALIBRATION CHAMBER

This application claims benefit of Provisional application Ser. No. 60/027,840 filed Oct. 4, 1996.

RIGHTS OF THE GOVERNMENT

The invention described herein may be manufactured and used by or for the Government of the United States for all governmental purposes without the payment of any royalty.

FIELD OF THE INVENTION

This invention relates to the art of calibrating pressure sensors and, more particularly, to an apparatus and method for calibrating catheter tip pressure transducers, which are employed for measuring blood pressure within a living body.

BACKGROUND OF THE INVENTION

Catheters have been used in the art for monitoring variations in blood pressure within a blood vessel, that is, within the cardiovascular system. Such catheters include those employing catheter tip transducers insertable into a blood vessel with the transducers providing direct pressure monitoring by transducing blood pressure at the region or regions of interest. Such catheter tip transducers may employ semiconductor material constructed and arranged with resistors and the like for use in developing an electrical signal representative of the monitored pressure and transmitting the signal by electrical conductors through the length of the catheter to monitoring systems located externally of the body of the subject being tested. Such monitoring systems usually display the subject's blood pressure wave form and also include a calibrated scale to give the pressure readouts in mm Hg. Typical monitoring systems include amplifiers, display devices and recording devices.

Examples of a single-sensor pressure measuring catheter are found in U.S. Pat. Nos. 4,274,423 and 4,722,348. The transducer disclosed in U.S. Pat. No. 4,274,423 includes a pressure sensor disposed within the end portion of a catheter. The pressure sensor takes the form of a pressure sensitive diaphragm constructed from a block of semiconductor material, such as silicon. The diaphragm is deflected in dependence upon the pressure and the deflection is sensed by one or more strain gauges located in the diaphragm. The strain gauges are connected by suitable conductors to a monitoring system which amplifies and displays the generated electrical signal. U.S. Pat. Nos. 4,809,704, 4,815,471 and 4,815,472 disclose multiple sensor pressure-measuring catheters with a plurality of pressure sensors spaced along the catheter.

Before a transducer such as those described above can be used, however, it must be calibrated with the monitoring system to ensure that the readings it produces are accurate. With prolonged use, transducers lose some sensitivity and become less accurate, thus making it necessary to calibrate the transducer to the monitoring system so that the monitoring system will be appropriately adjusted to compensate for such inaccuracy. Techniques have been devised in the prior art to ensure that the monitoring system reading corresponds to the transducer's sensitivity. Such techniques include electronic calibration procedures wherein the transducer end of the catheter is connected to an amplifier which contains circuitry which simulates transducer output voltages. A switch on the amplifier is activated and a voltage is produced which should be equivalent to the voltage produced by the transducer under ideal conditions. The disadvantage of this technique is that it does not take into account mechanical changes to the transducer, such as wear of the silicon diaphragm resulting from repeated use and protein build up resulting from insertion of the transducer into the living body. Such mechanical changes can result in inaccurate calibration of the transducer.

A second technique for calibration uses a syringe connected to one end of a section of tee-shaped tubing to provide an airtight chamber. The transducer end of the catheter is inserted into a second end of the tee and the output hose of a mercury manometer is inserted into the third end of the tee. A plunger is extended into the syringe barrel until the manometer indicates an appropriate calibration pressure, such as 100 mm Hg. Because of the tee connection, the transducer diaphragm is also subjected to the same pressure. Most likely, the monitoring system will indicate some pressure differing from that measured by the manometer due to the inaccuracy of the transducer. The monitoring system's sensitivity control must therefore be adjusted until it gives an accurate pressure reading. This procedure is repeated over a range of pressures to check linearity. Unfortunately, this method of calibration is susceptible to errors resulting from temperature effects and difficulty in sustaining a constant accurate pressure using the syringe.

It is, therefore, a principal object of the present invention to provide a novel apparatus and method for accomplishing accurate, repeatable calibrations of catheter tip pressure transducers while minimizing errors resulting from pressure leaks, temperature effects and mechanical changes to the transducer.

It is a feature of this invention to provide a novel system for calibration of single-sensor and dual-sensor catheter tip pressure transducers.

It is a further feature of this invention to provide a novel system for calibrating a plurality of catheter tip pressure transducers.

Other and further objects and features of the invention will become obvious to one skilled in the art upon an understanding of the illustrative embodiment about to be described and various advantages, not referred to herein, will occur to one skilled in the art upon employment of the invention in practice.

SUMMARY OF THE INVENTION

The present invention is directed to an apparatus for calibrating the pressure readings obtained by catheter tip pressure transducers. The apparatus includes a Plexiglas vessel covered by a closure containing eight catheter ports through which the transducers are introduced into the vessel. The vessel is filled with saline solution that has been warmed to body temperature. The transducer ends of the catheters are inserted through airtight hemostatic control valves into the vessel through the catheter ports. Plexiglas guide tubes are used to guide the transducers into the saline solution at predetermined distances below the fluid surface. These distances are used to calculate the hydrostatic pressures exerted upon the transducers by the saline solution. Known pressures are applied to the transducers through an airtight pressure port in the closure. Calculated hydrostatic pressures are added to the known pressures to provide calibration pressures for comparison with monitored pressure readings.

BRIEF DESCRIPTION OF THE DRAWINGS

FIG. 2 is an exploded cross sectional side view of a vessel and closure used in the calibration apparatus.

FIG. 3 is a top view of the closure showing catheter ports and a pressure port therethrough.

FIG. 4 is a top view of the closure showing stainless steel female lures attached to the catheter ports and pressure port.

DETAILED DESCRIPTION OF THE INVENTION

Figure 1:
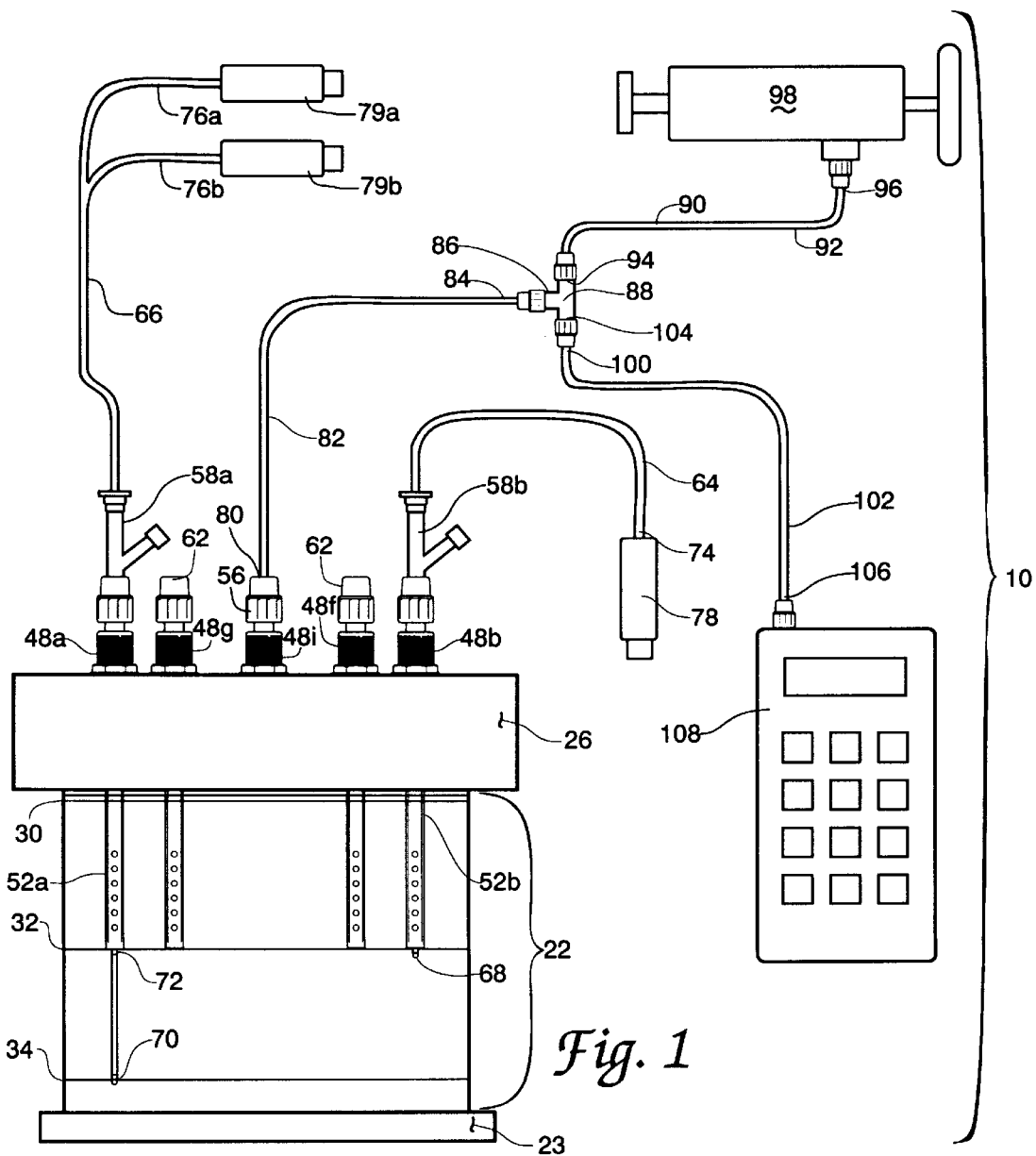
FIG. 1 illustrates a calibration apparatus constructed according to a preferred embodiment of the present invention.

A preferred embodiment of a pressure catheter calibration chamber in accordance with the present invention is illustrated at 10 in FIG. 1. Up to eight pressure catheters, single-sensor, dual-sensor, or a combination thereof, may be calibrated at one time using this invention. For the purposes of illustration only, it will be presumed that one single-sensor and one dual-sensor catheter are to be calibrated with the invention.

As shown in FIG. 1, pressure catheter calibration chamber 10 includes a vessel 22 having a unitary cylindrical body, which is preferably made from optically clear 0.25-inch thick Plexiglas, and an optically clear Plexiglas closure 26. Vessel 22 rests on a base 23. As best illustrated in FIG. 2, vessel 22 includes a threaded neck 24 which defines a cylindrical conduit having one end integral with vessel 22 and the other end defining an opening 28 through which a fluid may be introduced into vessel 22.

First 30, second 32 and third 34 horizontal lines are etched onto the outer surface 35 of the cylindrical vessel wall 36. These horizontal lines are used for establishing distances between fluid surface and transducers introduced into the fluid. The vertical distance between first horizontal line 30 and second horizontal line 32 is predetermined to be approximately 1.6875 inches or 0.0429 meters. The vertical distance between the second horizontal line 32 and third horizontal line 34 is predetermined to be approximately 1.1875 inches or 0.0302 meters.

Closure 26 includes a threaded portion which mates with threaded neck 24 to provide screw-type mounting of closure 26. As is conventionally known, closure 26 is unscrewed from neck 24 to introduce fluid into vessel 22. Closure 26 is subsequently screwed back onto neck 24 to re-seal vessel 22. Closure 26 also includes an o-ring 42 situated in a groove in closure 26 which provides an air-tight seal between closure 26 and vessel 22. Vessel 22, which is approximately 5.50 inches in inner diameter and approximately 6.00 inches in outer diameter, holds a total fluid volume of approximately 1 liter.

A fluid having similar physical properties as blood (for example, injectable saline, 0.9% sodium chloride solution) is introduced into vessel 22 through opening 28 so that the fluid level corresponds with first horizontal line 30. The vessel is then re-sealed by closure 26. In order to better simulate blood, the saline solution is warmed to body temperature (37° C.) before introduction into vessel 22.

As illustrated in FIG. 3, closure 26 includes eight catheter ports 44a–h and one pressure port 46. Catheter ports 44 define openings through closure 26 through which catheter tip pressure transducers may be introduced into the saline solution in vessel 22. Pressure port 46 defines an opening through closure 26 through which calibration pressures may be applied to transducers in vessel 22.

As best shown in FIG. 4, stainless steel female lures 48a–h are attached to catheter ports 44a–h at the top of closure 26. Stainless steel female lure 48i is attached to pressure port 46 at the top of closure 26.

Figure 5:
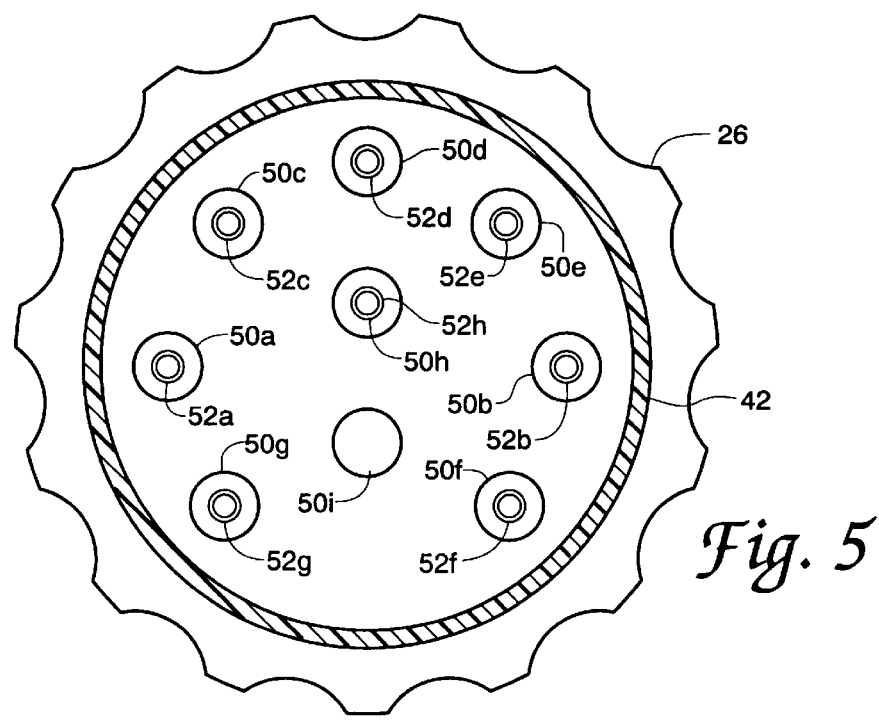
FIG. 5 is a bottom view of the closure showing hollow lower port connectors attached to the catheter ports and pressure port and hollow guide tubes attached to the hollow lower port connectors at the catheter ports.
Figure 6:
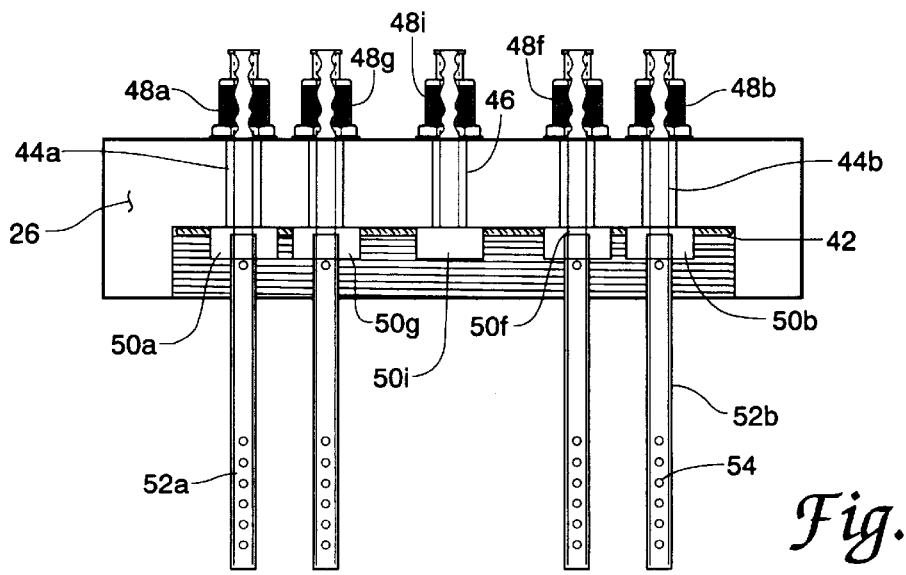
FIG. 6 is a cross sectional side view of the closure showing stainless steel female lures, catheter ports, pressure port, hollow lower port connectors and hollow guide tubes.

As illustrated in FIG. 5, hollow lower port connectors 50a–h are attached to catheter ports 44a–h at the bottom of closure 26. Hollow lower port connector 50i is attached to pressure port 46 at the bottom of closure 26. Hollow, clear Plexiglas guide tubes 52a–h are attached to lower port connectors 50a–h. As best illustrated in FIG. 6, each guide tube 52 contains small vent holes 54.

As shown in FIG. 1, hemostatic control valves 58a and 58b are attached to stainless steel female lures 48a and 48b. Single-sensor, or single-tipped, catheter 64 is passed through hemostatic control valve 58b and into vessel 22 through hollow guide tube 52b. Dual-sensor, or dual-tipped, catheter 66 is passed through hemostatic control valve 58a and into vessel 22 through hollow guide tube 52a. Hemostatic control valve 58b provides an air-tight seal between catheter 64 and closure 26. Hemostatic control valve 58a provides an air-tight seal between catheter 66 and closure 26. Guide tubes 52 provide means for guiding the transducer-ends of catheters 64 and 66 into the saline solution in vessel 22. Vent holes 54 in each guide tube 52 allow for fluid levels within vessel 22 and guide tubes 52 to equilibrate.

The transducer in single-tipped catheter 64 introduced into vessel 22 extends a vertical distance below first horizontal line 30. This vertical distance defines a single transducer placement point 68. For the dual-tipped catheter 66 introduced into vessel 22, the distal transducer extends a first vertical distance below first horizontal line 30 and the proximal transducer extends a second vertical distance below first horizontal line 30. This first vertical distance defines a distal transducer placement point 70 and the second vertical distance defines proximal transducer placement point 72.

Second horizontal line 32 identifies transducer placement point 68 and proximal transducer placement point 72. Thus, single-tipped catheter 64 should be introduced into vessel 22 so that transducer placement point 68 corresponds with second horizontal line 32. Dual-tipped catheter 66 should be introduced into vessel 22 so that proximal transducer placement point 72 corresponds with second horizontal line 32. By placing the transducers at these points, the height of the fluid above the transducers is predetermined to be 0.0429 meters, the distance between first 30 and second 32 horizontal lines.

Third horizontal line 34 identifies distal transducer placement point 70. Thus, dual-tipped catheter 66 should be introduced into vessel 22 so that distal transducer placement point 70 corresponds with third horizontal line 34. By placing the transducer at this point, the height of the fluid above the transducer is predetermined to be 0.0731 meters, the distance between first 30 and third 34 horizontal lines.

Catheter port caps 62 are attached to stainless steel female lures 48c–h and seal unused catheter ports 44c–h.

The second end 74 of single-tipped catheter 64 is attached to electrical connector 78. The second end of dual-tipped catheter 66 is bifurcated into first section 76a, which is attached to electrical connector 79a, and second section 76b, which is attached to electrical connector 79b. Electrical connectors 78, 79a and 79b are connected to amplifiers (not shown). The amplifiers are connected to monitors, stripchart recorders and analog recording systems (not shown).

The means for introducing known pressures to the transducers is illustrated in FIG. 1. A high pressure tubing connector 56 is attached to stainless steel female lure 48i. A first end 80 of a first section of high pressure tubing 82 is attached to connector tubing 56 and the second end 84 is attached to a first opening 86 of a high pressure tubing tee section 88. A first end 90 of a second section of high pressure tubing 92 is attached to a second opening 94 of the high pressure tubing tee 88 and the second end 96 is attached to a pressure pump 98. A first end 100 of a third section of tubing 102 is attached to the third end 104 of the tee 88 and the second end 106 is attached to a digital pressure manometer 108. Pressure pump 98 produces known pressures which are applied to the transducers in catheters 64 and 66 in vessel 22. Known pressures are measured by digital pressure manometer 108.

The hydrostatic pressure exerted upon each transducer by the fluid is calculated by the following formula: hydrostatic pressure=density of fluid×gravity×height of fluid above transducer (or vertical distance which transducer extends below the fluid line). For the transducer in single-tipped catheter 64, and for the proximal transducer in dual-tipped catheter 66, where the fluid is saline solution, the hydrostatic pressure=1000 kg/m$^3$ (density of fluid)×9.80 m/s$^2$ (gravity)× 0.04 m (fluid height, or predetermined distance between first horizontal line and second horizontal line)=392 kg/ms$^2$=392 Pa. Hydrostatic pressure=392 Pa÷133 N/m$^2$=2.95 mm Hg. For the distal transducer in dual-tipped catheter 66, where the fluid is saline solution, the hydrostatic pressure=1000 kg/m$^3$ (density of fluid)×9.80 M/s$^2$ (gravity)×0.07 m (fluid height or predetermined distance between first horizontal line and third horizontal line)=686 kg/ms$^2$=686 Pa. Hydrostatic pressure=686 Pa÷133 N/m$^2$=5.16 mm Hg.

For each transducer, a calibration pressure is determined by adding the calculated hydrostatic pressure to an applied known pressure. This calibration pressure is then compared to the monitored pressure and the monitoring system is adjusted as necessary to match the calibration pressure. This procedure is repeated over a range of known pressures to check linearity.

The teachings of all patents, journal articles and other references cited herein are incorporated herein by reference. It is understood that modifications to the invention may be made as might occur to one with skill in the field of the invention within the scope of the appended claims. All embodiments contemplated thereunder which achieve the objects of the invention have therefore not been shown in complete detail. Other embodiments may be developed without departing from the spirit of the invention or from the scope of the appended claims.

We claim:

1. An apparatus for calibrating at least one pressure-sensing catheter, said catheter having at least one transducer supported on a first end for detecting blood pressure pulses, comprising:

(a) a vessel having an opening for introducing a fluid into said vessel, said fluid defining a horizontal fluid level line within said vessel;

(b) a removable closure means for said opening;

(c) at least one catheter port corresponding to each said catheter, said catheter port defined through said closure means through which said transducer on said first end of said corresponding catheter may be introduced into said fluid in said vessel;

(d) means for providing an airtight seal between said catheter and said corresponding catheter port;

(e) a pressure port defined through said closure means through which at least one known pressure may be introduced on said transducer;

(f) means for introducing said known pressure through said pressure port on said transducer; and (g) means for measuring the hydrostatic pressure exerted upon said transducer by said fluid.

2. The apparatus according to claim 1, wherein said means for providing an airtight seal between said catheter and said corresponding catheter port includes at least one hemostatic valve corresponding to each said catheter port, said hemostatic valve attached to said corresponding catheter port such that said first end of said catheter may be introduced through said hemostatic valve and through said corresponding catheter port into said fluid in said vessel.

3. The apparatus according to claim 1, further comprising means for guiding said first end of said catheter into said fluid in said vessel.

4. The apparatus according to claim 3, wherein said means for guiding said first end of said catheter includes at least one hollow tube corresponding to each said catheter port, said hollow tube attached to said corresponding catheter port and extending downward from said corresponding catheter port into said fluid such that said first end of said catheter may be introduced through said corresponding catheter port into said hollow tube, said hollow tube having holes for equilibrating fluid levels within said hollow tube and said vessel.

5. An apparatus according to claim 1, wherein said means for introducing said known pressure includes a first section of high pressure tubing extending between said pressure port and a first opening of a high pressure tubing tee, a second section of high pressure tubing extending between a second opening of said high pressure tubing tee and a pressure pump, and a third section of high pressure tubing extending between a third opening of said high pressure tubing tee and a manometer, such that said pump produces said known pressure and said manometer measures said known pressure.

6. An apparatus according to claim 1, wherein said catheter supports one transducer on said first end and said transducer extends a predetermined vertical distance Y below said fluid level line and wherein said means for measuring said hydrostatic pressure includes first and second horizontal lines etched on an outer surface of the walls of said vessel, said vessel walls being non-opaque, such that said first horizontal line corresponds with said fluid level line and said second horizontal line extends said vertical distance Y below said first horizontal line, whereby said hydrostatic pressure is determined according to the formula: hydrostatic pressure=(D)(G)(Y); where D is the density of said fluid and G is gravity.

7. An apparatus according to claim 1, wherein said catheter supports a distal transducer at a first location on said first end and a proximal transducer at a second location on said first end and said distal transducer extends a first predetermined vertical distance Y1 below said fluid level line and said proximal transducer extends a second predetermined vertical distance Y2 below said fluid level line and wherein said means for measuring said hydrostatic pressure includes first, second and third horizontal lines etched on an outer surface of the walls of said vessel, said vessel walls being non-opaque, such that said first horizontal line corresponds with said fluid level line, said second horizontal line extends said second vertical distance Y2 below said first horizontal line and said third horizontal line extends said first vertical distance Y1 below said horizontal line and whereby said hydrostatic pressure exerted on said distal transducer is determined according to the formula: hydrostatic pressure=(D)(G)(Y1) and said hydrostatic pressure exerted on said proximal transducer is determined according to the formula: hydrostatic pressure=(D)(G)(Y2); where D is the density of said fluid and G is gravity.

8. The apparatus of claim 1, wherein said vessel is fabricated from Plexiglas.

9. The apparatus of claim 1, wherein said vessel is cylindrical in shape.

10. The method of calibrating at least one pressure sensing catheter, said catheter having at least one transducer supported on a first end for detecting blood pressure pulses and an electrical connector at a second end for transmitting data from said transducer to an external monitoring system, said method comprising the steps of:

(a) introducing a fluid into a vessel, said fluid defining a horizontal fluid level line within said vessel;

(b) covering said vessel with a removable closure;

(c) inserting said first end of said catheter through a catheter port located in said closure amidst a hemostatic valve and immersing said transducer in said fluid such that said transducer extends a predetermined distance Y below said fluid level line;

(d) introducing at least one known pressure on said transducer through a pressure port located in said closure by activating a pressure pump and a manometer;

(e) adding the hydrostatic pressure exerted upon said transducer by said fluid to said known pressure thereby arriving at a calibration pressure, said hydrostatic pressure determined according to the formula: hydrostatic pressure=(D)(G)(Y); where D is the density of said fluid and G is gravity, and;

(f) comparing said calibration pressure with the pressure indication provided by said external monitoring system.

11. The method of claim 10, in which said fluid is injectable saline, 0.9% sodium chloride solution.

12. The method of claim 10, in which said fluid is warmed to body temperature prior to being introduced into said vessel.

* * * * *